US012569671B2

(12) United States Patent     (10) Patent No.:   US 12,569,671 B2

Schellenberg et al.     (45) Date of Patent:    Mar. 10, 2026

(54) DEVICE AND METHOD FOR DETERMINATION OF A CARDIAC OUTPUT FOR A CARDIAC ASSISTANCE SYSTEM

(71) Applicant: KARDION GMBH, Stuttgart (DE)

(72) Inventors: Inga Schellenberg, Stuttgart (DE); Thomas Alexander Schlebusch, Renningen (DE); Tobias Schmid, Stuttgart (DE)

(73) Assignee: KARDION GMBH, Stuttgart (DE)

( * ) Notice: Subject to any disclaimer, the term of this patent is extended or adjusted under 35 U.S.C. 154(b) by 1059 days.

(21) Appl. No.: 15/734,841

(22) PCT Filed: Jun. 6, 2019

(86) PCT No.: PCT/EP2019/064783
§ 371 (c)(1),
(2) Date: Jun. 18, 2021

(87) PCT Pub. No.: WO2019/234152
PCT Pub. Date: Dec. 12, 2019

(65) Prior Publication Data
US 2021/0379359 A1    Dec. 9, 2021

(30) Foreign Application Priority Data

Jun. 6, 2018   (DE) ......................... 102018208931.0

(51) Int. Cl.
*A61M 60/523*    (2021.01)
*A61B 5/00*    (2006.01)
(Continued)

(52) U.S. Cl.
CPC ........ *A61M 60/523* (2021.01); *A61M 60/178* (2021.01); *A61M 60/216* (2021.01);
(Continued)

(58) Field of Classification Search
CPC .............. A61M 60/523; A61M 60/178; A61M 60/216; A61M 60/515; A61M 60/816;
(Continued)

(56) References Cited

U.S. PATENT DOCUMENTS 3,088,323 A   5/1963   Welkowitz et al.
4,023,562 A   5/1977   Hynecek et al.
(Continued)

FOREIGN PATENT DOCUMENTS

CA   3 122 415    7/2020
CN   1192351 A    9/1998
(Continued)

OTHER PUBLICATIONS

"Understanding Hot-Wire Anemometry," Advanced Thermal Solutions, Inc. (2007) (Year: 2007).*
(Continued)

*Primary Examiner* — Jennifer Pitrak McDonald
*Assistant Examiner* — Christopher J Mutchler
(74) *Attorney, Agent, or Firm* — Knobbe, Martens, Olson & Bear, LLP

(57) ABSTRACT

The invention relates to a device (105) for determining a cardiac output for a cardiac assist system (100), wherein the device (105) comprises a support structure (115) and a sensor device (120). The support structure (115) comprises at least one brace (125) and a connection section (130) for connecting the device (105) to an element (110, 112) of the cardiac assist system (100). The at least one brace (125) is connected to the connection section (130) and can be folded away from the element (110, 112). The sensor device (120) is coupled to the at least one brace (125) and configured to sense a blood stream.

19 Claims, 3 Drawing Sheets

(51) Int. Cl.

| | |
|---|---|
| *A61B 5/026* | (2006.01) |
| *A61B 8/00* | (2006.01) |
| *A61B 8/06* | (2006.01) |
| *A61B 8/08* | (2006.01) |
| *A61B 8/12* | (2006.01) |
| *A61M 60/178* | (2021.01) |
| *A61M 60/216* | (2021.01) |
| *A61M 60/515* | (2021.01) |
| *A61M 60/816* | (2021.01) |
| *A61M 60/861* | (2021.01) |

(52) U.S. Cl.
CPC ........ *A61M 60/515* (2021.01); *A61M 60/816* (2021.01); *A61M 60/861* (2021.01); *A61M 2205/0266* (2013.01); *A61M 2205/3334* (2013.01); *A61M 2205/3368* (2013.01); *A61M 2205/36* (2013.01); *A61M 2210/125* (2013.01)

(58) Field of Classification Search
CPC ........ A61M 60/861; A61M 2205/0266; A61M 2205/3334; A61M 2205/3368; A61M 2205/36; A61M 2210/125; A61M 2205/3331; A61B 5/026; A61B 8/065; A61B 8/0883; A61B 8/12; A61B 8/4416; A61B 5/6847; A61B 5/6869; A61B 8/06; A61B 5/6876; A61B 8/488

See application file for complete search history.

(56) References Cited

U.S. PATENT DOCUMENTS

| | | | |
|---|---|---|---|
| 4,559,952 A | 12/1985 | Angelsen et al. | |
| 4,680,730 A | 7/1987 | Omoda | |
| 4,781,525 A | 11/1988 | Hubbard et al. | |
| 4,888,011 A | 12/1989 | Kung et al. | |
| 4,889,131 A | 12/1989 | Salem et al. | |
| 4,902,272 A | 2/1990 | Milder et al. | |
| 5,045,051 A | 9/1991 | Milder et al. | |
| 5,269,811 A | 12/1993 | Hayes | |
| 5,289,821 A | 3/1994 | Swartz | |
| 5,456,715 A | 10/1995 | Liotta | |
| 5,527,159 A | 6/1996 | Bozeman, Jr. et al. | |
| 5,581,038 A | 12/1996 | Lampropoulos | |
| 5,606,972 A | 3/1997 | Routh | |
| 5,613,935 A | 3/1997 | Jarvik | |
| 5,662,115 A | 9/1997 | Torp | |
| 5,676,651 A * | 10/1997 | Larson, Jr. .......... | A61M 60/237 |
| | | | 604/33 |
| 5,720,771 A | 2/1998 | Snell | |
| 5,752,976 A | 5/1998 | Duffin et al. | |
| 5,766,207 A | 6/1998 | Potter et al. | |
| 5,827,203 A | 10/1998 | Nita | |
| 5,865,759 A | 2/1999 | Koblanski | |
| 5,888,242 A | 3/1999 | Antaki et al. | |
| 5,904,708 A | 5/1999 | Goedeke | |
| 5,911,685 A | 6/1999 | Siess et al. | |
| 5,964,694 A | 10/1999 | Siess et al. | |
| 5,980,465 A | 11/1999 | Elgas | |
| 6,007,478 A | 12/1999 | Siess et al. | |
| 6,024,704 A | 2/2000 | Meador et al. | |
| 6,053,873 A * | 4/2000 | Govari ................. | A61B 5/0031 |
| | | | 600/468 |
| 6,167,765 B1 | 1/2001 | Weitzel | |
| 6,176,822 B1 | 1/2001 | Nix et al. | |
| 6,183,412 B1 | 2/2001 | Benkowsi et al. | |
| 6,185,460 B1 | 2/2001 | Thompson | |
| 6,190,324 B1 | 2/2001 | Kieval et al. | |
| 6,210,318 B1 | 4/2001 | Lederman | |
| 6,231,498 B1 | 5/2001 | Pfeiffer et al. | |
| 6,245,007 B1 | 6/2001 | Bedingham et al. | |
| 6,314,322 B1 | 11/2001 | Rosenberg | |
| 6,351,048 B1 | 2/2002 | Schob et al. | |
| 6,398,734 B1 | 6/2002 | Cimochowski et al. | |

| | | | |
|---|---|---|---|
| 6,432,136 B1 | 8/2002 | Weiss et al. | |
| 6,438,409 B1 | 8/2002 | Malik et al. | |
| 6,512,949 B1 | 1/2003 | Combs et al. | |
| 6,530,876 B1 | 3/2003 | Spence | |
| 6,540,658 B1 | 4/2003 | Fasciano et al. | |
| 6,540,659 B1 | 4/2003 | Milbocker | |
| 6,561,975 B1 | 5/2003 | Pool et al. | |
| 6,579,257 B1 | 6/2003 | Elgas et al. | |
| 6,602,182 B1 | 8/2003 | Milbocker | |
| 6,605,032 B2 | 8/2003 | Benkowsi et al. | |
| 6,652,447 B2 | 11/2003 | Benkowsi et al. | |
| 6,731,976 B2 | 5/2004 | Penn et al. | |
| 6,879,126 B2 | 4/2005 | Paden et al. | |
| 6,912,423 B2 | 6/2005 | Ley et al. | |
| 6,949,066 B2 | 9/2005 | Bearnson et al. | |
| 6,984,201 B2 | 1/2006 | Khaghani et al. | |
| 7,010,954 B2 | 3/2006 | Siess | |
| 7,022,100 B1 | 4/2006 | Aboul-Hosn et al. | |
| 7,024,244 B2 | 4/2006 | Muhlenberg et al. | |
| 7,070,555 B2 | 7/2006 | Siess | |
| 7,083,588 B1 | 8/2006 | Shmulewitz et al. | |
| 7,138,776 B1 | 11/2006 | Gauthier et al. | |
| 7,160,243 B2 | 1/2007 | Medvedev | |
| 7,175,588 B2 | 2/2007 | Morello | |
| 7,177,681 B2 | 2/2007 | Xhu | |
| 7,238,151 B2 | 7/2007 | Frazier | |
| 7,396,327 B2 | 7/2008 | Morello | |
| 7,513,864 B2 | 4/2009 | Kantrowitz et al. | |
| 7,520,850 B2 | 4/2009 | Brockway | |
| 7,526,338 B1 | 4/2009 | Gill | |
| 7,527,599 B2 | 5/2009 | Hickey | |
| 7,591,777 B2 | 9/2009 | LaRose | |
| 7,744,560 B2 | 6/2010 | Struble | |
| 7,794,384 B2 | 9/2010 | Sugiura et al. | |
| 7,819,916 B2 | 10/2010 | Yaegashi | |
| 7,850,593 B2 | 12/2010 | Vincent et al. | |
| 7,850,594 B2 | 12/2010 | Sutton et al. | |
| 7,856,335 B2 | 12/2010 | Morello et al. | |
| 7,862,501 B2 | 1/2011 | Woodward et al. | |
| 7,951,062 B2 | 5/2011 | Morello | |
| 7,951,129 B2 | 5/2011 | Chinchoy | |
| 7,963,905 B2 | 6/2011 | Salmonsen et al. | |
| 7,988,728 B2 | 8/2011 | Ayre | |
| 8,075,472 B2 | 12/2011 | Zilbershlag et al. | |
| 8,190,390 B2 | 5/2012 | Morello et al. | |
| 8,211,028 B2 | 7/2012 | Karamanoglu et al. | |
| 8,303,482 B2 | 11/2012 | Schima et al. | |
| 8,323,173 B2 | 12/2012 | Benkowsi et al. | |
| 8,435,182 B1 | 5/2013 | Tamura | |
| 8,449,444 B2 | 5/2013 | Poirier | |
| 8,545,380 B2 | 10/2013 | Farnan et al. | |
| 8,585,572 B2 | 11/2013 | Mehmanesh | |
| 8,591,393 B2 | 11/2013 | Walters et al. | |
| 8,594,790 B2 | 11/2013 | Kjellstrom et al. | |
| 8,622,949 B2 | 1/2014 | Zafirelis et al. | |
| 8,657,733 B2 | 2/2014 | Ayre et al. | |
| 8,657,875 B2 | 2/2014 | Kung et al. | |
| 8,715,151 B2 | 5/2014 | Poirier | |
| 8,747,293 B2 | 6/2014 | Arndt et al. | |
| 8,849,398 B2 | 9/2014 | Evans | |
| 8,864,643 B2 | 10/2014 | Reichenbach et al. | |
| 8,864,644 B2 | 10/2014 | Yomtov | |
| 8,876,685 B2 | 11/2014 | Crosby et al. | |
| 8,882,477 B2 | 11/2014 | Fritz, IV et al. | |
| 8,888,728 B2 | 11/2014 | Aboul-Hosn et al. | |
| 8,897,873 B2 | 11/2014 | Schima et al. | |
| 8,903,492 B2 | 12/2014 | Soykan et al. | |
| 9,091,271 B2 | 7/2015 | Bourque | |
| 9,297,735 B2 | 3/2016 | Graichen et al. | |
| 9,308,305 B2 | 4/2016 | Chen et al. | |
| 9,345,824 B2 | 5/2016 | Mohl et al. | |
| 9,371,826 B2 | 6/2016 | Yanai et al. | |
| 9,427,508 B2 | 8/2016 | Reyes et al. | |
| 9,427,509 B2 | 8/2016 | Vodermayer | |
| 9,474,840 B2 | 10/2016 | Siess | |
| 9,492,601 B2 | 11/2016 | Casas et al. | |
| 9,511,179 B2 | 12/2016 | Casas et al. | |
| 9,555,173 B2 | 1/2017 | Spanier | |
| 9,555,175 B2 | 1/2017 | Bulent et al. | |

(56) References Cited

U.S. PATENT DOCUMENTS

| | | | |
|---|---|---|---|
| 9,556,873 B2 | 1/2017 | Yanai et al. |
| 9,566,374 B2 | 2/2017 | Spence et al. |
| 9,636,442 B2 | 5/2017 | Karmon et al. |
| 9,656,010 B2 | 5/2017 | Burke |
| 9,669,142 B2 | 6/2017 | Spanier et al. |
| 9,669,144 B2 | 6/2017 | Spanier et al. |
| 9,694,123 B2 | 7/2017 | Bourque et al. |
| 9,713,701 B2 | 7/2017 | Sarkar et al. |
| 9,744,282 B2 | 8/2017 | Rosenberg et al. |
| 9,789,236 B2 | 10/2017 | Bonde |
| 9,833,550 B2 | 12/2017 | Siess |
| 9,848,899 B2 | 12/2017 | Sliwa et al. |
| 9,849,224 B2 | 12/2017 | Angwin et al. |
| 9,878,087 B2 | 1/2018 | Richardson et al. |
| 9,943,236 B2 | 4/2018 | Bennett et al. |
| 9,950,102 B2 | 4/2018 | Spence et al. |
| 9,974,894 B2 | 5/2018 | Morello |
| 9,999,714 B2 | 6/2018 | Spanier et al. |
| 10,010,662 B2 | 7/2018 | Wiesener et al. |
| 10,022,480 B2 | 7/2018 | Greatrex et al. |
| 10,029,037 B2 | 7/2018 | Muller et al. |
| 10,052,420 B2 | 8/2018 | Medvedev et al. |
| 10,279,093 B2 | 5/2019 | Reichenbach et al. |
| 10,322,217 B2 | 6/2019 | Spence |
| 10,342,906 B2 | 7/2019 | D'Ambrosio et al. |
| 10,350,342 B2 | 7/2019 | Thomas et al. |
| 10,357,598 B2 | 7/2019 | Aboul-Hosn et al. |
| 10,376,162 B2 | 8/2019 | Edelman et al. |
| 10,413,651 B2 | 9/2019 | Yomtov et al. |
| 10,426,879 B2 | 10/2019 | Farnan |
| 10,449,275 B2 | 10/2019 | Corbett |
| 10,500,322 B2 | 12/2019 | Karch |
| 10,525,178 B2 | 1/2020 | Zeng |
| 10,549,020 B2 | 2/2020 | Spence et al. |
| 10,561,771 B2 | 2/2020 | Heilman et al. |
| 10,561,772 B2 | 2/2020 | Schumacher |
| 10,561,773 B2 | 2/2020 | Ferrari et al. |
| 10,632,241 B2 | 4/2020 | Schenck et al. |
| 10,660,998 B2 | 5/2020 | Hodges |
| 10,668,195 B2 | 6/2020 | Flores |
| 10,732,583 B2 | 8/2020 | Rudser |
| 10,857,275 B2 | 12/2020 | Granegger |
| 10,864,308 B2 | 12/2020 | Muller et al. |
| 11,027,114 B2 | 6/2021 | D'Ambrosio et al. |
| RE48,649 E | 7/2021 | Siess |
| 11,067,085 B2 | 7/2021 | Granegger et al. |
| 11,120,908 B2 | 9/2021 | Agnello et al. |
| 11,131,968 B2 | 9/2021 | Rudser |
| 11,147,960 B2 | 10/2021 | Spanier et al. |
| 11,154,701 B2 | 10/2021 | Reyes et al. |
| 11,154,702 B2 | 10/2021 | Kadrolkar et al. |
| 11,185,682 B2 | 11/2021 | Farnan |
| 11,191,945 B2 | 12/2021 | Siess et al. |
| 11,197,618 B2 | 12/2021 | Edelman et al. |
| 11,217,344 B2 | 1/2022 | Agnello |
| 11,235,139 B2 | 2/2022 | Kudlik |
| 11,241,572 B2 | 2/2022 | Dague et al. |
| 11,273,299 B2 | 3/2022 | Wolman et al. |
| 11,285,310 B2 | 3/2022 | Curran et al. |
| 11,285,311 B2 | 3/2022 | Siess et al. |
| 11,298,524 B2 | 4/2022 | El Katerji et al. |
| 11,311,711 B2 | 4/2022 | Casas et al. |
| 11,316,679 B2 | 4/2022 | Agnello |
| 11,320,382 B2 | 5/2022 | Aikawa |
| 11,324,395 B2 | 5/2022 | Banik et al. |
| 11,331,082 B2 | 5/2022 | Itoh et al. |
| 11,337,724 B2 | 5/2022 | Masubuchi et al. |
| 11,338,125 B2 | 5/2022 | Liu et al. |
| 11,351,356 B2 | 6/2022 | Mohl |
| 11,351,357 B2 | 6/2022 | Mohl |
| 11,351,358 B2 | 6/2022 | Nix et al. |
| 11,357,438 B2 | 6/2022 | Stewart et al. |
| 11,357,968 B2 | 6/2022 | El Katerji et al. |
| 11,376,415 B2 | 7/2022 | Mohl |
| 11,376,419 B2 | 7/2022 | Reyes et al. |
| 11,389,639 B2 | 7/2022 | Casas |
| 11,389,641 B2 | 7/2022 | Nguyen et al. |
| 11,413,444 B2 | 8/2022 | Nix et al. |
| 11,413,445 B2 | 8/2022 | Brown et al. |
| 11,420,041 B2 | 8/2022 | Karch |
| 11,439,806 B2 | 9/2022 | Kimball et al. |
| 11,446,481 B2 | 9/2022 | Wolman et al. |
| 11,478,629 B2 | 10/2022 | Harjes et al. |
| 11,517,740 B2 | 12/2022 | Agarwa et al. |
| 11,521,723 B2 | 12/2022 | Liu et al. |
| 11,524,165 B2 | 12/2022 | Tan et al. |
| 11,527,322 B2 | 12/2022 | Agnello et al. |
| 11,529,062 B2 | 12/2022 | Moyer et al. |
| 11,554,260 B2 | 1/2023 | Reyes et al. |
| 11,572,879 B2 | 2/2023 | Mohl |
| 11,574,741 B2 | 2/2023 | Tan et al. |
| 11,577,068 B2 | 2/2023 | Spence et al. |
| 11,581,083 B2 | 2/2023 | El Katerji et al. |
| 11,583,659 B2 | 2/2023 | Pfeffer et al. |
| 11,587,337 B2 | 2/2023 | Lemay et al. |
| 11,590,337 B2 | 2/2023 | Granegger et al. |
| 11,622,695 B1 | 4/2023 | Adriola et al. |
| 11,628,293 B2 | 4/2023 | Gandhi et al. |
| 11,639,722 B2 | 5/2023 | Medvedev et al. |
| 11,648,386 B2 | 5/2023 | Poirer |
| 11,653,841 B2 | 5/2023 | Reyes et al. |
| 11,666,746 B2 | 6/2023 | Ferrari et al. |
| 11,668,321 B2 | 6/2023 | Richert et al. |
| 11,674,517 B2 | 6/2023 | Mohl |
| 11,676,718 B2 | 6/2023 | Agnello et al. |
| 11,684,276 B2 | 6/2023 | Cros et al. |
| 11,684,769 B2 | 6/2023 | Harjes et al. |
| 11,694,539 B2 | 7/2023 | Kudlik et al. |
| 11,694,813 B2 | 7/2023 | El Katerji et al. |
| 11,696,782 B2 | 7/2023 | Carlson et al. |
| 11,707,617 B2 | 7/2023 | Reyes et al. |
| 11,712,167 B2 | 8/2023 | Medvedev et al. |
| 11,724,091 B2 | 8/2023 | Siess et al. |
| 11,754,077 B1 | 9/2023 | Mohl |
| D1,001,145 S | 10/2023 | Lussier et al. |
| D1,001,146 S | 10/2023 | Lussier et al. |
| 11,771,885 B2 | 10/2023 | Liu et al. |
| 11,779,234 B2 | 10/2023 | Harjes et al. |
| 11,781,551 B2 | 10/2023 | Yanai et al. |
| 11,790,487 B2 | 10/2023 | Barbato et al. |
| 11,793,994 B2 | 10/2023 | Josephy et al. |
| 11,806,116 B2 | 11/2023 | Tuval et al. |
| 11,806,517 B2 | 11/2023 | Petersen |
| 11,806,518 B2 | 11/2023 | Michelena et al. |
| 11,813,079 B2 | 11/2023 | Lau et al. |
| 11,818,782 B2 | 11/2023 | Doudian et al. |
| 11,824,381 B2 | 11/2023 | Conyers et al. |
| 11,826,127 B2 | 11/2023 | Casas |
| 11,832,793 B2 | 12/2023 | McWeeney et al. |
| 11,832,868 B2 | 12/2023 | Smail et al. |
| 11,837,364 B2 | 12/2023 | Lee et al. |
| 11,844,592 B2 | 12/2023 | Tuval et al. |
| 11,844,940 B2 | 12/2023 | D'Ambrosio et al. |
| 11,850,073 B2 | 12/2023 | Wright et al. |
| 11,850,414 B2 | 12/2023 | Schenck et al. |
| 11,850,415 B2 | 12/2023 | Schwammenthal et al. |
| D1,012,284 S | 1/2024 | Glaser et al. |
| 11,857,345 B2 | 1/2024 | Hanson et al. |
| 11,864,878 B2 | 1/2024 | Duval et al. |
| 11,872,384 B2 | 1/2024 | Cotter |
| 11,883,207 B2 | 1/2024 | El Katerji et al. |
| D1,014,552 S | 2/2024 | Lussier et al. |
| 11,890,082 B2 | 2/2024 | Cros et al. |
| 11,896,199 B2 | 2/2024 | Lent et al. |
| 11,900,660 B2 | 2/2024 | Saito et al. |
| 11,903,657 B2 | 2/2024 | Geric et al. |
| 11,906,411 B2 | 2/2024 | Graichen et al. |
| 11,911,550 B2 | 2/2024 | Itamochi et al. |
| D1,017,634 S | 3/2024 | Lussier et al. |
| D1,017,699 S | 3/2024 | Moore et al. |
| 11,923,078 B2 | 3/2024 | Fallen et al. |
| 11,923,093 B2 | 3/2024 | Moffitt et al. |
| 11,925,794 B2 | 3/2024 | Malkin et al. |
| 11,931,073 B2 | 3/2024 | Walsh et al. |

(56) References Cited

U.S. PATENT DOCUMENTS

| | | |
|---|---|---|
| 11,931,528 B2 | 3/2024 | Rohl et al. |
| 11,931,588 B2 | 3/2024 | Aghassian |
| 11,986,274 B2 | 5/2024 | Edelman |
| 12,017,076 B2 | 6/2024 | Tan et al. |
| 12,023,476 B2 | 7/2024 | Tuval et al. |
| 12,029,891 B2 | 7/2024 | Siess et al. |
| 12,059,559 B2 | 8/2024 | Muller et al. |
| D1,043,730 S | 9/2024 | Lussier et al. |
| D1,043,731 S | 9/2024 | Lussier et al. |
| 12,076,544 B2 | 9/2024 | Siess et al. |
| 12,097,016 B2 | 9/2024 | Goldvasser |
| 12,102,815 B2 | 10/2024 | Dhaliwal et al. |
| 12,144,650 B2 | 11/2024 | Spanier et al. |
| 12,144,976 B2 | 11/2024 | Baumbach et al. |
| 12,178,554 B2 | 12/2024 | Stotz et al. |
| 12,179,009 B2 | 12/2024 | El Katerji et al. |
| 12,183,459 B2 | 12/2024 | Agnello et al. |
| 12,194,287 B2 | 1/2025 | Kassel et al. |
| 12,201,821 B2 | 1/2025 | Schlebusch et al. |
| 12,211,615 B2 | 1/2025 | Nix et al. |
| D1,060,379 S | 2/2025 | Lussier et al. |
| 12,213,771 B2 | 2/2025 | Curran et al. |
| 12,217,850 B2 | 2/2025 | Agnello |
| 12,222,267 B2 | 2/2025 | Stotz et al. |
| 12,251,551 B2 | 3/2025 | Liu et al. |
| 12,257,424 B2 | 3/2025 | Schlebusch et al. |
| 12,268,861 B2 | 4/2025 | D'Ambrosio et al. |
| 12,296,158 B2 | 5/2025 | Higgins et al. |
| 12,296,159 B2 | 5/2025 | Schilling et al. |
| 12,310,621 B2 | 5/2025 | Murphy |
| 12,310,708 B2 | 5/2025 | Schlebusch et al. |
| 12,311,160 B2 | 5/2025 | Schlebusch et al. |
| 12,324,906 B2 | 6/2025 | Baumbach et al. |
| 12,329,501 B2 | 6/2025 | Moyer et al. |
| 12,329,956 B2 | 6/2025 | Sunagawa |
| 12,329,959 B2 | 6/2025 | Hassan et al. |
| 12,343,518 B2 | 7/2025 | Tuval et al. |
| D1,090,610 S | 8/2025 | Kroeker et al. |
| 12,377,256 B2 | 8/2025 | Stotz et al. |
| 12,390,168 B2 | 8/2025 | Katerji et al. |
| 12,397,099 B2 | 8/2025 | Germain et al. |
| D1,092,492 S | 9/2025 | Lussier et al. |
| 12,409,313 B2 | 9/2025 | Eggen et al. |
| 2001/0016686 A1 | 8/2001 | Okada et al. |
| 2001/0037093 A1 | 11/2001 | Benkowski et al. |
| 2001/0039828 A1 | 11/2001 | Shin et al. |
| 2002/0022785 A1 | 2/2002 | Romano |
| 2002/0082585 A1 | 6/2002 | Carroll et al. |
| 2002/0093412 A1 | 7/2002 | Morrison |
| 2002/0147495 A1 | 10/2002 | Petroff |
| 2002/0151761 A1 | 10/2002 | Viole et al. |
| 2003/0069465 A1 | 4/2003 | Benkowski et al. |
| 2003/0130581 A1 | 7/2003 | Salo et al. |
| 2003/0139643 A1 | 7/2003 | Smith et al. |
| 2003/0167002 A1 | 9/2003 | Nagar et al. |
| 2003/0191357 A1 | 10/2003 | Frazier |
| 2003/0199727 A1 | 10/2003 | Burke |
| 2004/0022640 A1 | 2/2004 | Siess et al. |
| 2004/0044266 A1 | 3/2004 | Siess et al. |
| 2004/0065143 A1 | 4/2004 | Husher |
| 2004/0124979 A1 | 7/2004 | Medema |
| 2004/0130009 A1 | 7/2004 | Tangpuz |
| 2004/0167376 A1 | 8/2004 | Peters et al. |
| 2004/0167410 A1 | 8/2004 | Hettrick |
| 2004/0225177 A1* | 11/2004 | Coleman ............ A61M 60/148 600/17 |
| 2004/0241019 A1 | 12/2004 | Goldowsky |
| 2004/0260346 A1 | 12/2004 | Overall et al. |
| 2005/0001324 A1 | 1/2005 | Dunn |
| 2005/0019167 A1 | 1/2005 | Nusser et al. |
| 2005/0107658 A1 | 5/2005 | Brockway |
| 2005/0126268 A1 | 6/2005 | Ouriev et al. |
| 2005/0267322 A1 | 12/2005 | LaRose |
| 2006/0030809 A1 | 2/2006 | Barzilay et al. |
| 2006/0108697 A1 | 5/2006 | Wang |
| 2006/0108901 A1 | 5/2006 | Mao-Chin |
| 2006/0122583 A1 | 6/2006 | Pesach et al. |
| 2006/0196277 A1 | 9/2006 | Allen et al. |
| 2006/0229488 A1 | 10/2006 | Ayre et al. |
| 2006/0287600 A1 | 12/2006 | McEowen |
| 2006/0287604 A1 | 12/2006 | Hickey |
| 2007/0060787 A1 | 3/2007 | Peters et al. |
| 2007/0069354 A1 | 3/2007 | Dangelmaier |
| 2007/0073352 A1 | 3/2007 | Euler et al. |
| 2007/0088214 A1 | 4/2007 | Shuros et al. |
| 2007/0156006 A1 | 7/2007 | Smith et al. |
| 2007/0255352 A1 | 11/2007 | Roline et al. |
| 2007/0266778 A1 | 11/2007 | Corey et al. |
| 2007/0282209 A1 | 12/2007 | Lui et al. |
| 2007/0299325 A1 | 12/2007 | Farrell et al. |
| 2008/0015517 A1 | 1/2008 | Geistert et al. |
| 2008/0082005 A1 | 4/2008 | Stern et al. |
| 2008/0091239 A1 | 4/2008 | Johansson et al. |
| 2008/0097595 A1* | 4/2008 | Gabbay ............. A61B 17/3417 604/532 |
| 2008/0102096 A1 | 5/2008 | Molin et al. |
| 2008/0108901 A1 | 5/2008 | Baba et al. |
| 2008/0108930 A1 | 5/2008 | Weitzel et al. |
| 2008/0133006 A1 | 6/2008 | Crosby et al. |
| 2008/0146996 A1 | 6/2008 | Smisson |
| 2008/0210016 A1 | 9/2008 | Zwirn et al. |
| 2008/0248614 A1 | 10/2008 | Yang |
| 2008/0262289 A1 | 10/2008 | Goldowsky |
| 2008/0262361 A1 | 10/2008 | Gutfinger et al. |
| 2008/0269822 A1 | 10/2008 | Ljungstrom et al. |
| 2008/0275339 A1 | 11/2008 | Thiemann et al. |
| 2008/0287799 A1 | 11/2008 | Hall |
| 2008/0306328 A1 | 12/2008 | Ercolani |
| 2009/0024042 A1 | 1/2009 | Nunez et al. |
| 2009/0025459 A1 | 1/2009 | Zhang et al. |
| 2009/0064755 A1 | 3/2009 | Fleischli et al. |
| 2009/0105799 A1 | 4/2009 | Hekmat et al. |
| 2009/0131765 A1 | 5/2009 | Roschak et al. |
| 2009/0204163 A1 | 8/2009 | Shuros et al. |
| 2009/0226328 A1 | 9/2009 | Morello |
| 2009/0312650 A1 | 12/2009 | Maile et al. |
| 2010/0010354 A1 | 1/2010 | Skerl et al. |
| 2010/0082099 A1 | 4/2010 | Vodermayer et al. |
| 2010/0087742 A1 | 4/2010 | Bishop et al. |
| 2010/0160801 A1 | 6/2010 | Takatani et al. |
| 2010/0219967 A1 | 9/2010 | Kaufmann |
| 2010/0222632 A1 | 9/2010 | Poirier |
| 2010/0222633 A1 | 9/2010 | Poirier |
| 2010/0222635 A1 | 9/2010 | Poirier |
| 2010/0222878 A1 | 9/2010 | Poirier |
| 2010/0268017 A1 | 10/2010 | Siess |
| 2010/0298625 A1 | 11/2010 | Reichenbach et al. |
| 2010/0324378 A1 | 12/2010 | Tran et al. |
| 2011/0004075 A1 | 1/2011 | Stahmann et al. |
| 2011/0022057 A1 | 1/2011 | Eigler et al. |
| 2011/0071336 A1 | 3/2011 | Yomtov |
| 2011/0144744 A1* | 6/2011 | Wampler ............ A61M 60/422 623/3.13 |
| 2011/0160516 A1 | 6/2011 | Dague |
| 2011/0172505 A1 | 7/2011 | Kim |
| 2011/0184301 A1 | 7/2011 | Holmstrom |
| 2011/0186943 A1 | 8/2011 | Pahl |
| 2011/0218435 A1 | 9/2011 | Srinivasan et al. |
| 2011/0230068 A1 | 9/2011 | Pahl |
| 2012/0022645 A1 | 1/2012 | Burke |
| 2012/0029408 A1 | 2/2012 | Beaudin |
| 2012/0084024 A1 | 4/2012 | Norcross, Jr. |
| 2012/0150089 A1 | 6/2012 | Penka et al. |
| 2012/0150291 A1 | 6/2012 | Aber |
| 2012/0197141 A1* | 8/2012 | Vanney ................ A61B 8/06 600/505 |
| 2012/0203476 A1 | 8/2012 | Dam |
| 2012/0245404 A1 | 9/2012 | Smith |
| 2012/0247200 A1 | 10/2012 | Ahonen et al. |
| 2012/0310037 A1 | 12/2012 | Choi et al. |
| 2012/0330214 A1 | 12/2012 | Peters et al. |
| 2013/0041204 A1 | 2/2013 | Heilman et al. |
| 2013/0046129 A1 | 2/2013 | Medvedev et al. |
| 2013/0066141 A1 | 3/2013 | Doerr et al. |

(56) References Cited

U.S. PATENT DOCUMENTS

| | | | |
|---|---|---|---|
| 2013/0072846 A1 | 3/2013 | Heide et al. | |
| 2013/0116575 A1 | 5/2013 | Mickle et al. | |
| 2013/0144379 A1 | 6/2013 | Najafi et al. | |
| 2013/0289334 A1 | 10/2013 | Badstibner | |
| 2013/0289376 A1 | 10/2013 | Lang | |
| 2013/0303831 A1 | 11/2013 | Evans | |
| 2013/0304404 A1 | 11/2013 | Dam | |
| 2014/0005467 A1 | 1/2014 | Farnan et al. | |
| 2014/0013852 A1 | 1/2014 | Brown et al. | |
| 2014/0030122 A1 | 1/2014 | Ozaki | |
| 2014/0100414 A1 | 4/2014 | Tamez et al. | |
| 2014/0114202 A1 | 4/2014 | Hein et al. | |
| 2014/0128659 A1 | 5/2014 | Heuring et al. | |
| 2014/0200389 A1 | 7/2014 | Yanai et al. | |
| 2014/0243688 A1 | 8/2014 | Caron et al. | |
| 2014/0275720 A1 | 9/2014 | Ferrari | |
| 2014/0275727 A1 | 9/2014 | Bonde | |
| 2014/0296677 A1 | 10/2014 | McEowen | |
| 2014/0303426 A1 | 10/2014 | Kerkhoffs et al. | |
| 2014/0342203 A1 | 11/2014 | Elian | |
| 2015/0032007 A1 | 1/2015 | Ottevanger et al. | |
| 2015/0080743 A1 | 3/2015 | Siess | |
| 2015/0141832 A1 | 5/2015 | Yu et al. | |
| 2015/0141842 A1 | 5/2015 | Spanier et al. | |
| 2015/0157216 A1 | 6/2015 | Stigall et al. | |
| 2015/0174307 A1 | 6/2015 | Eckman et al. | |
| 2015/0190092 A1 | 7/2015 | Mori | |
| 2015/0196076 A1 | 7/2015 | Billingslea | |
| 2015/0201900 A1 | 7/2015 | Syed | |
| 2015/0250935 A1* | 9/2015 | Anderson | A61M 60/865 |
| | | | 600/16 |
| 2015/0273184 A1 | 10/2015 | Scott et al. | |
| 2015/0290372 A1* | 10/2015 | Muller | A61M 60/174 |
| | | | 600/16 |
| 2015/0306290 A1 | 10/2015 | Rosenberg et al. | |
| 2015/0306291 A1 | 10/2015 | Bonde et al. | |
| 2015/0307344 A1 | 10/2015 | Ernst | |
| 2015/0327921 A1 | 11/2015 | Govari | |
| 2015/0335804 A1 | 11/2015 | Marseille et al. | |
| 2015/0365738 A1 | 12/2015 | Purvis et al. | |
| 2016/0000983 A1 | 1/2016 | Mohl et al. | |
| 2016/0008531 A1 | 1/2016 | Wang et al. | |
| 2016/0022889 A1 | 1/2016 | Bluvshtein et al. | |
| 2016/0022890 A1 | 1/2016 | Schwammenthal et al. | |
| 2016/0045165 A1 | 2/2016 | Braido et al. | |
| 2016/0095968 A1 | 4/2016 | Rudser | |
| 2016/0101230 A1 | 4/2016 | Ochsner et al. | |
| 2016/0144166 A1 | 5/2016 | Decréet al. | |
| 2016/0151553 A1 | 6/2016 | Bonde | |
| 2016/0166747 A1 | 6/2016 | Frazier et al. | |
| 2016/0213828 A1 | 7/2016 | Sievers | |
| 2016/0250399 A1 | 9/2016 | Tiller et al. | |
| 2016/0278856 A1 | 9/2016 | Panescu | |
| 2016/0302672 A1 | 10/2016 | Kuri | |
| 2016/0303299 A1* | 10/2016 | Muller | A61M 60/174 |
| 2016/0317043 A1 | 11/2016 | Campo | |
| 2016/0338629 A1 | 11/2016 | Doerr | |
| 2017/0010144 A1 | 1/2017 | Lenner et al. | |
| 2017/0021070 A1 | 1/2017 | Petersen | |
| 2017/0049945 A1 | 2/2017 | Halvorsen et al. | |
| 2017/0086780 A1 | 3/2017 | Sokulin et al. | |
| 2017/0098491 A1 | 4/2017 | Ziaie et al. | |
| 2017/0112985 A1 | 4/2017 | Yomtov | |
| 2017/0128646 A1 | 5/2017 | Karch | |
| 2017/0136164 A1 | 5/2017 | Yeatts | |
| 2017/0202575 A1 | 7/2017 | Stanfield et al. | |
| 2017/0224279 A1 | 8/2017 | Cahan et al. | |
| 2017/0239407 A1 | 8/2017 | Hayward | |
| 2017/0258980 A1 | 9/2017 | Katsuki et al. | |
| 2017/0348470 A1* | 12/2017 | D'Ambrosio | A61M 60/174 |
| 2017/0354812 A1 | 12/2017 | Callaghan et al. | |
| 2018/0064860 A1 | 3/2018 | Nunez et al. | |
| 2018/0078159 A1 | 3/2018 | Edelman et al. | |
| 2018/0093070 A1 | 4/2018 | Cottone | |
| 2018/0110910 A1 | 4/2018 | Rodemerk et al. | |
| 2018/0126053 A1 | 5/2018 | Zilbershlag et al. | |
| 2018/0199635 A1 | 7/2018 | Longinotti-Buitoni et al. | |
| 2018/0250457 A1 | 9/2018 | Morello et al. | |
| 2018/0256796 A1 | 9/2018 | Hansen | |
| 2018/0256800 A1 | 9/2018 | Conyers et al. | |
| 2018/0264182 A1 | 9/2018 | Spanier et al. | |
| 2018/0280598 A1 | 10/2018 | Curran et al. | |
| 2018/0316209 A1 | 11/2018 | Gliner | |
| 2018/0326131 A1 | 11/2018 | Muller et al. | |
| 2018/0333059 A1 | 11/2018 | Casas | |
| 2018/0353667 A1 | 12/2018 | Moyer et al. | |
| 2018/0369469 A1 | 12/2018 | Le Duc De Lillers et al. | |
| 2019/0001038 A1 | 1/2019 | Yomtov et al. | |
| 2019/0054223 A1 | 2/2019 | Frazier et al. | |
| 2019/0083690 A1 | 3/2019 | Siess et al. | |
| 2019/0192752 A1 | 6/2019 | Tiller et al. | |
| 2019/0192753 A1 | 6/2019 | Liu et al. | |
| 2019/0209755 A1 | 7/2019 | Nix et al. | |
| 2019/0209758 A1 | 7/2019 | Tuval et al. | |
| 2019/0216995 A1 | 7/2019 | Kapur et al. | |
| 2019/0217002 A1 | 7/2019 | Urakabe | |
| 2019/0223877 A1 | 7/2019 | Nitzen et al. | |
| 2019/0240680 A1 | 8/2019 | Hayakawa | |
| 2019/0254543 A1 | 8/2019 | Hartholt et al. | |
| 2019/0282741 A1 | 9/2019 | Franano et al. | |
| 2019/0282744 A1 | 9/2019 | D'Ambrosio et al. | |
| 2019/0351117 A1 | 11/2019 | Cambronne et al. | |
| 2019/0351118 A1 | 11/2019 | Graichen et al. | |
| 2020/0016309 A1 | 1/2020 | Kallenbach et al. | |
| 2020/0028376 A1 | 1/2020 | Ha | |
| 2020/0038567 A1 | 2/2020 | Siess et al. | |
| 2020/0060559 A1 | 2/2020 | Edelman et al. | |
| 2020/0069857 A1 | 3/2020 | Schwammenthal et al. | |
| 2020/0147283 A1 | 5/2020 | Tanner et al. | |
| 2020/0164125 A1 | 5/2020 | Muller et al. | |
| 2020/0164126 A1 | 5/2020 | Muller | |
| 2020/0253583 A1 | 8/2020 | Brisken et al. | |
| 2020/0312450 A1 | 10/2020 | Agnello et al. | |
| 2021/0268264 A1 | 9/2021 | Stotz | |
| 2021/0290087 A1 | 9/2021 | Schlebusch | |
| 2021/0290930 A1 | 9/2021 | Kasel | |
| 2021/0290933 A1 | 9/2021 | Stotz | |
| 2021/0339002 A1 | 11/2021 | Schlebusch et al. | |
| 2021/0339004 A1 | 11/2021 | Schlebusch et al. | |
| 2021/0346674 A1 | 11/2021 | Baumbach et al. | |
| 2021/0346675 A1 | 11/2021 | Schlebusch et al. | |
| 2021/0346676 A1 | 11/2021 | Schlebusch et al. | |
| 2021/0346677 A1 | 11/2021 | Baumbach et al. | |
| 2021/0346678 A1 | 11/2021 | Baumbach et al. | |
| 2021/0378523 A1 | 12/2021 | Budde | |
| 2021/0379360 A1 | 12/2021 | Schellenberg | |
| 2021/0393944 A1 | 12/2021 | Wenning | |
| 2022/0016411 A1 | 1/2022 | Winterwerber | |
| 2022/0032032 A1 | 2/2022 | Schlebusch et al. | |
| 2022/0032036 A1 | 2/2022 | Baumbach et al. | |
| 2022/0039669 A1 | 2/2022 | Schlebusch et al. | |
| 2022/0047173 A1 | 2/2022 | Stotz et al. | |
| 2022/0050037 A1 | 2/2022 | Stotz et al. | |
| 2022/0072298 A1 | 3/2022 | Spanier et al. | |
| 2022/0076807 A1 | 3/2022 | Agnello | |
| 2022/0079457 A1 | 3/2022 | Tuval et al. | |
| 2022/0105339 A1 | 4/2022 | Nix et al. | |
| 2022/0126085 A1 | 4/2022 | Farnan | |
| 2022/0126086 A1 | 4/2022 | Schlebusch et al. | |
| 2022/0142462 A1 | 5/2022 | Douk et al. | |
| 2022/0161019 A1 | 5/2022 | Mitze et al. | |
| 2022/0361762 A1 | 11/2022 | Lalancette | |
| 2023/0173250 A1 | 6/2023 | Stigloher | |
| 2023/0191141 A1 | 6/2023 | Wenning et al. | |
| 2024/0011808 A1 | 1/2024 | Winzer et al. | |
| 2024/0074828 A1 | 3/2024 | Wenning | |
| 2024/0245902 A1 | 7/2024 | Schlebusch et al. | |
| 2025/0032773 A1 | 1/2025 | Baumbach et al. | |
| 2025/0121177 A1 | 4/2025 | West | |
| 2025/0143587 A1 | 5/2025 | Stotz | |
| 2025/0144397 A1 | 5/2025 | Kassel et al. | |
| 2025/0222247 A1 | 7/2025 | Schlebusch | |

(56)  References Cited

U.S. PATENT DOCUMENTS

| | | |
|---|---|---|
| 2025/0235687 A1 | 7/2025 | Schlebusch et al. |
| 2025/0251330 A1 | 8/2025 | Stotz |
| 2025/0281060 A1 | 9/2025 | Schlebusch et al. |

FOREIGN PATENT DOCUMENTS

| | | |
|---|---|---|
| CN | 1222862 A | 7/1999 |
| CN | 1202871 C | 5/2005 |
| CN | 1661338 A | 8/2005 |
| CN | 101128168 | 2/2008 |
| CN | 101208045 | 6/2008 |
| CN | 101214158 | 7/2008 |
| CN | 101351237 | 1/2009 |
| CN | 101448535 | 6/2009 |
| CN | 101460094 | 6/2009 |
| CN | 101579233 | 11/2009 |
| CN | 201437016 | 4/2010 |
| CN | 101711683 | 5/2010 |
| CN | 201658687 | 12/2010 |
| CN | 102421372 | 4/2012 |
| CN | 102803923 | 11/2012 |
| CN | 103328018 | 9/2013 |
| CN | 103857326 | 6/2014 |
| CN | 103957957 | 7/2014 |
| CN | 104105449 | 10/2014 |
| CN | 104188687 | 12/2014 |
| CN | 106104229 | 11/2016 |
| CN | 106333707 | 1/2017 |
| CN | 206007680 | 3/2017 |
| CN | 107530479 | 1/2018 |
| CN | 107632167 | 1/2018 |
| CN | 109939282 | 6/2019 |
| CN | 209790495 | 12/2019 |
| CN | 210020563 | 2/2020 |
| CN | 215841206 | 2/2022 |
| CN | 217828630 | 11/2022 |
| CN | 219250364 | 6/2023 |
| CN | 118320294 | 7/2024 |
| CN | 113769260 | 9/2024 |
| CN | 118920928 | 11/2024 |
| DE | 195 20 920 | 12/1995 |
| DE | 198 21 307 | 10/1999 |
| DE | 100 59 714 | 5/2002 |
| DE | 100 60 275 | 6/2002 |
| DE | 101 44 269 | 3/2003 |
| DE | 102 26 305 | 10/2003 |
| DE | 10 2006 001 180 | 9/2007 |
| DE | 10 2009 007 216 | 8/2010 |
| DE | 10 2009 011 726 | 9/2010 |
| DE | 10 2009 025 464 | 1/2011 |
| DE | 10 2009 047 845 | 3/2011 |
| DE | 10 2011 106 142 | 12/2012 |
| DE | 20 2011 110 389 | 9/2013 |
| DE | 10 2015 004 177 | 10/2015 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2018 208 536 | 12/2019 |
| DE | 10 2018 208 862 | 12/2019 |
| DE | 10 2018 208 916 | 12/2019 |
| DE | 10 2018 208 927 | 12/2019 |
| DE | 10 2018 208 945 | 12/2019 |
| DE | 10 2018 210 076 | 12/2019 |
| DE | 10 2018 212 153 | 1/2020 |
| DE | 10 2018 213 151 | 2/2020 |
| DE | 10 2018 213 350 | 2/2020 |
| DE | 10 2018 220 658 | 6/2020 |
| DE | 10 2018 222 505 | 6/2020 |
| DE | 10 2020 102 473 | 8/2021 |
| DE | 11 2020 003 151 | 3/2022 |
| EP | 0 794 411 | 9/1997 |
| EP | 0 916 359 | 5/1999 |
| EP | 1 062 959 | 12/2000 |
| EP | 1 339 443 | 11/2001 |
| EP | 1 011 803 | 9/2004 |
| EP | 1 354 606 | 6/2006 |
| EP | 2 143 385 | 1/2010 |
| EP | 2 175 770 | 4/2010 |
| EP | 2 187 807 | 6/2012 |
| EP | 2 570 143 | 3/2013 |
| EP | 2 401 003 | 10/2013 |
| EP | 1 871 441 | 11/2014 |
| EP | 2 859 911 | 4/2015 |
| EP | 2 213 227 | 8/2016 |
| EP | 2 835 141 | 8/2016 |
| EP | 3 088 016 | 11/2016 |
| EP | 2 585 129 | 3/2017 |
| EP | 2 945 661 | 11/2017 |
| EP | 2 136 861 | 12/2017 |
| EP | 3 020 426 | 12/2017 |
| EP | 3 287 154 | 2/2018 |
| EP | 3 205 359 | 8/2018 |
| EP | 3 205 360 | 8/2018 |
| EP | 3 378 421 | 9/2018 |
| EP | 3 478 333 | 5/2019 |
| EP | 3 389 738 | 8/2019 |
| EP | 2 505 090 | 12/2019 |
| EP | 3 668 560 | 6/2020 |
| EP | 3 720 520 | 10/2020 |
| EP | 3 753 594 | 12/2020 |
| EP | 3 357 523 | 1/2021 |
| EP | 3 490 628 | 2/2021 |
| EP | 3 487 548 | 3/2021 |
| EP | 3 509 661 | 3/2021 |
| EP | 3 515 523 | 3/2021 |
| EP | 3 528 863 | 3/2021 |
| EP | 3 615 103 | 3/2021 |
| EP | 4 271 461 | 3/2021 |
| EP | 3 131 600 | 6/2021 |
| EP | 3 131 615 | 6/2021 |
| EP | 3 463 505 | 9/2021 |
| EP | 3 884 970 | 9/2021 |
| EP | 2 599 510 | 10/2021 |
| EP | 3 003 421 | 10/2021 |
| EP | 3 027 241 | 10/2021 |
| EP | 3 668 561 | 10/2021 |
| EP | 3 164 168 | 12/2021 |
| EP | 3 344 129 | 12/2021 |
| EP | 3 624 867 | 3/2022 |
| EP | 3 651 822 | 3/2022 |
| EP | 3 689 389 | 3/2022 |
| EP | 3 737 436 | 3/2022 |
| EP | 3 972 661 | 3/2022 |
| EP | 3 984 589 | 4/2022 |
| EP | 3 654 006 | 5/2022 |
| EP | 3 737 310 | 7/2022 |
| EP | 2 999 400 | 8/2022 |
| EP | 3 711 788 | 8/2022 |
| EP | 3 694 573 | 9/2022 |
| EP | 3 600 477 | 10/2022 |
| EP | 3 897 768 | 10/2022 |
| EP | 2 892 583 | 1/2023 |
| EP | 3 370 797 | 1/2023 |
| EP | 3 597 231 | 1/2023 |
| EP | 3 668 562 | 1/2023 |
| EP | 3 856 275 | 1/2023 |
| EP | 3 003 420 | 2/2023 |
| EP | 3 397 299 | 2/2023 |
| EP | 3 046 594 | 3/2023 |
| EP | 3 938 005 | 4/2023 |
| EP | 3 685 562 | 5/2023 |
| EP | 3 397 298 | 7/2023 |
| EP | 3 809 959 | 7/2023 |
| EP | 2 072 150 | 9/2023 |
| EP | 2 961 984 | 9/2023 |
| EP | 3 352 808 | 9/2023 |
| EP | 3 768 156 | 9/2023 |
| EP | 4 052 754 | 10/2023 |
| EP | 3 157 596 | 11/2023 |
| EP | 3 766 428 | 11/2023 |
| EP | 3 781 027 | 11/2023 |
| EP | 4 061 470 | 11/2023 |

(56) References Cited

FOREIGN PATENT DOCUMENTS

| | | |
| --- | --- | --- |
| EP | 4 070 720 | 11/2023 |
| EP | 3 449 958 | 12/2023 |
| EP | 3 687 596 | 12/2023 |
| EP | 3 768 340 | 12/2023 |
| EP | 3 801 675 | 1/2024 |
| EP | 3 566 636 | 2/2024 |
| EP | 3 634 526 | 2/2024 |
| EP | 3 768 347 | 2/2024 |
| EP | 3 790 606 | 2/2024 |
| EP | 3 930 780 | 2/2024 |
| EP | 3 397 147 | 3/2024 |
| EP | 3 782 695 | 3/2024 |
| EP | 3 854 448 | 3/2024 |
| EP | 4 140 532 | 5/2024 |
| EP | 3 693 038 | 6/2024 |
| EP | 3 970 765 | 7/2024 |
| EP | 3 854 444 | 9/2024 |
| EP | 3 793 674 | 10/2024 |
| EP | 3 618 885 | 11/2024 |
| EP | 4 034 221 | 11/2024 |
| EP | 3 809 960 | 12/2024 |
| EP | 3 854 446 | 2/2025 |
| EP | 4 429 754 | 2/2025 |
| EP | 3 970 785 | 3/2025 |
| EP | 4 429 753 | 3/2025 |
| EP | 3 950 043 | 5/2025 |
| EP | 3 899 964 | 6/2025 |
| EP | 3 948 888 | 6/2025 |
| EP | 3 965 845 | 6/2025 |
| EP | 4 039 319 | 6/2025 |
| EP | 4 297 672 | 7/2025 |
| EP | 3 668 559 | 8/2025 |
| EP | 3 848 088 | 8/2025 |
| EP | 4 218 556 | 9/2025 |
| ES | 2 913 485 | 6/2022 |
| JP | S59-080229 | 5/1984 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | H02-234750 | 9/1990 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-052489 | 2/1998 |
| JP | H10-505766 | 6/1998 |
| JP | H11-239617 | 9/1999 |
| JP | 2000-512191 | 9/2000 |
| JP | 2001-037728 | 2/2001 |
| JP | 2001-506140 | 5/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2004-515278 | 5/2004 |
| JP | 2005-028137 | 2/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2006-518249 | 8/2008 |
| JP | 2008-178690 | 8/2008 |
| JP | 2009-504290 | 2/2009 |
| JP | 2009-240348 | 10/2009 |
| JP | 2010-518907 | 6/2010 |
| JP | 2012-520157 | 9/2012 |
| JP | 2013-128792 | 7/2013 |
| JP | 2014-524274 | 9/2014 |
| JP | 2015-514529 | 5/2015 |
| JP | 2015-514531 | 5/2015 |
| JP | 2015-515429 | 5/2015 |
| JP | 2015-122448 | 7/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2017-500932 | 1/2017 |
| JP | 2017-176719 | 10/2017 |
| JP | 2017-532084 | 11/2017 |
| JP | 2019-523110 | 8/2019 |
| JP | 2020-072985 | 5/2020 |
| WO | WO 89/006513 | 1/1989 |
| WO | WO 92/015239 | 9/1992 |
| WO | WO 94/009835 | 5/1994 |
| WO | WO 98/043688 | 10/1998 |
| WO | WO 00/033047 | 6/2000 |
| WO | WO 2006/122001 | 11/2006 |
| WO | WO 2010/142286 | 12/2010 |
| WO | WO 2010/143272 | 12/2010 |
| WO | WO 2012/018917 | 2/2012 |
| WO | WO 2012/112378 | 8/2012 |
| WO | WO 2013/160443 | 10/2013 |
| WO | WO 2014/042925 | 3/2014 |
| WO | WO 2014/141284 | 9/2014 |
| WO | WO 2014/165635 | 10/2014 |
| WO | WO 2015/085220 | 6/2015 |
| WO | WO 2016/001284 | 1/2016 |
| WO | WO 2016/066180 | 5/2016 |
| WO | WO 2016/137743 | 9/2016 |
| WO | WO 2017/032751 | 3/2017 |
| WO | WO 2017/066257 | 4/2017 |
| WO | WO 2017/106190 | 6/2017 |
| WO | WO 2017/147291 | 8/2017 |
| WO | WO 2017/214118 | 12/2017 |
| WO | WO 2018/005228 | 1/2018 |
| WO | WO 2018/048800 | 3/2018 |
| WO | WO 2018/109038 | 6/2018 |
| WO | WO 2018/213089 | 11/2018 |
| WO | WO 2019/013794 | 1/2019 |
| WO | WO 2019/034670 | 2/2019 |
| WO | WO 2019/034775 | 2/2019 |
| WO | WO 2019/078723 | 4/2019 |
| WO | WO 2019/126721 | 6/2019 |
| WO | WO 2019/137911 | 7/2019 |
| WO | WO 2019/193604 | 10/2019 |
| WO | WO 2019/219883 | 11/2019 |
| WO | WO 2019/229210 | 12/2019 |
| WO | WO 2019/229220 | 12/2019 |
| WO | WO 2019/234145 | 12/2019 |
| WO | WO 2019/234146 | 12/2019 |
| WO | WO 2019/234148 | 12/2019 |
| WO | WO 2019/234149 | 12/2019 |
| WO | WO 2019/234151 | 12/2019 |
| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/243582 | 12/2019 |
| WO | WO 2020/030686 | 2/2020 |
| WO | WO 2020/030706 | 2/2020 |
| WO | WO 2020/064707 | 4/2020 |
| WO | WO 2020/089429 | 5/2020 |
| WO | WO 2020/198280 | 10/2020 |
| WO | WO 2020/243756 | 12/2020 |
| WO | WO 2023/040546 | 12/2021 |
| WO | WO 2022/074136 | 4/2022 |
| WO | WO 2022/109590 | 5/2022 |
| WO | WO 2022/173970 | 8/2022 |
| WO | WO 2023/226779 | 9/2022 |

(56)                 References Cited

FOREIGN PATENT DOCUMENTS

| | | |
|---|---|---|
| WO | WO 2023/049813 | 3/2023 |
| WO | WO 2024/104184 | 5/2024 |

OTHER PUBLICATIONS

Hertz Ph.D. et al., "Ultrasonic Engineering in Heart Diagnosis", The American Journal of Cardiology, Jan. 1967, vol. 19, No. 1, pp. 6-17.

International Preliminary Report on Patentability and Written Opinion received in PCT Application No. PCT/EP2019/064783, dated Dec. 17, 2020 in 8 pages.

International Search Report and Written Opinion received in PCT Application No. PCT/EP2019/064783, dated Oct. 17, 2019 in 12 pages.

Kong et al., "A Stein Equation Approach for Solutions to the Diophantine Equations," 2010 Chinese Control and Decision Conference, Xuzhou, May 26, 2010, pp. 3024-3028.

Koseli et al., "Online Viscosity Measurement of Complex Solutions Using Ultrasound Doppler Velocimetry", Turk J Chem, Jan. 2006, vol. 30, pp. 297-305.

McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.

Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.

Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.

Atkinson et al., "Pulse-Doppler Ultrasound and Its Clinical Application", The Yale Journal of Biology and Medicine, 1977, vol. 50, pp. 367-373.

Leguy et al., "Assessment of Blood Volume Flow in Slightly Curved Arteries from a Single Velocity Profile", Journal of Biomechanics, 2009, pp. 1664-1672.

Lombardi et al., "Flow Rate Profiler: an instrument to measure blood velocity profiles", Ultrasonics, 2001, vol. 39, pp. 143-150.

Mushi et al., "Identification of Fluidic Element Models to Simulate the Short-Term Baroreflex", Proceedings of the 45th IEEE Conference on Decision & Control, San Diego, CA, Dec. 13-15, 2006, pp. 6.

Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.

Vieli, A., "Doppler Flow Determination", BJA: British Journal of Anaesthesia, 1988, vol. 60, pp. 107S-112S.

Vollkron et al., "Advanced Suction Detection for an Axial Flow Pump", Artificial Organs, 2006, vol. 30, No. 9, pp. 665-670.

Vollkron et al., "Development of a Suction Detection System for Axial Blood Pumps", Artificial Organs, 2004, vol. 28, No. 8, pp. 709-716.

Yuanyuan et al., "Characteristics Analysis for Doppler Ultrasound Blood Flow Signals", China Medical Device Information, 5(1), Feb. 28, 1999, pp. 36-42.

Zhang, Dabiao et al., "Design of Microwave Velocity and Distance Monitor System", Instrument Technique and Sensor, Hebei Normal University, Apr. 25, 2004, pp. 3.

Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.

HeartMate 3™ Left Ventricular Assist System, Instructions for Use, Thoratec Corporation, Aug. 2017, pp. 536. [Uploaded in 3 parts].

Tan et al., "Surface Engineering and Patterning Using Parylene for Biological Applications." Materials, Mar. 15, 2010, vol. 3, No. 3, pp. 1803-1832.

Chung et al., "Improved Efficiency Characteristics of Wireless Power Charging System for Superconducting MAGLEV Train Using Inserted Permanent Magnets," 2018 IEEE International Symposium on Electromagnetic Compatibility, 2018, pp. 564-567.

"ECG Electrodes product comparison chart," 3M.com, 2018, https://multimedia.3m.com/mws/media/14908830/red-dot-ecg-electrodes-comparison-chart.pdf, accessed May 18, 2025, 1 page.

Eeckhout, MD, PhD, et al., "Handbook of Complications During Percutaneous Cardiovascular Interventions", 2007 Informa UK Ltd., Ch. 12, pp. 167-177.

Mack-Haynes, Robin, "Fasteners Made Easy," New Mexico State University, https://pubs.nmsu.edu/_c/C232.pdf, accessed May 18, 2025, pp. 8.

Mullins, Charles E., MD, "Cardiac Catheterization in Congenital Heart Disease: Pediatric and Adult", Blackwell Futura, 2006, Chapters 3, 4 and 32, pp. 101.

Radiologyinfo.org, "Subcutaneous Port," Definition, https://www.radiologyinfo.org/en/glossary?id=ezNFREEzNEFFLTI5OTAtNDVFNy04MkVBLTA1RDVGMDdBMzNFRH0=&i=1&b=0&modal=1, accessed Sep. 2, 2025, 1 page.

Sigg et al., "Cardiac Electophysiology Methods and Models", Springer, Clinical Perspective: Electrophysiology in the Young and Patients with Congenital Heart Disease, Ch. 23, 2010, pp. 457-477.

Walser, Eric, "Venous access ports: indications, implantation technique, follow-up, and complications;" Cardiovasc Intervent Radial, Aug. 2012; vol. 35, No. 4, pp. 751-764. (Abstract Only).

* cited by examiner

DEVICE AND METHOD FOR DETERMINATION OF A CARDIAC OUTPUT FOR A CARDIAC ASSISTANCE SYSTEM

BACKGROUND

Field

The invention is based on a device or a method for determining a cardiac output of a patient.

Description of the Related Art

In order to determine the cardiac output of a patient with an implanted cardiac assist system, for example a left ventricular cardiac assist system, it is possible to measure a pump volume flow by correlating operating parameters of the cardiac assist system. US 2005/0215843 A1 describes such a method. In addition, physiological parameters such as blood pressure can also be taken into account, as described in US 2014/0100414 A1. Both approaches measure the pump volume flow, i.e. a blood flow generated by the cardiac assist system.

SUMMARY

The invention is based on the task to optimize a device and a method for determining a cardiac output for a cardiac assist system, in particular also with regard to the arrangement and use of sensors.

In light of this background, the approach presented here proposes a device for determining a cardiac output for a cardiac assist system, a cardiac assist system, and a method for determining a cardiac output according to the main claims. Advantageous further developments and improvements of the device specified in the independent claim are possible using the measures specified in the dependent claims.

The approach presented here can be used to determine the cardiac output of a patient with an implanted cardiac assist system, for example a left ventricular cardiac assist system. This approach can advantageously not only be used to measure the pump volume flow generated by the cardiac assist system, but also to account for residual cardiac output in order to determine the patient's total cardiac output. The approach presented here can also advantageously be used in conjunction with a cardiac assist system for minimally invasive insertion as a fully implanted system.

A device for determining a cardiac output for a cardiac assist system is presented. The device comprises a support structure and a sensor device. The support structure comprises at least one brace and a connection section for connecting the device to an element of the cardiac assist system. The at least one brace is connected to the connection section and can be moved away or folded away from the element. The sensor device is coupled to the support structure and is formed to sense a blood stream.

Cardiac output is the volume of blood that is pumped by the heart per unit of time and, in the case of a cardiac assist system, additionally or alternatively pumped by the cardiac assist system. The cardiac assist system can be a heart pump such as a ventricular assist system, for example a left ventricular assist system (LVAD). The support structure can for example be formed as a carrier structure for the sensor device. Additionally or alternatively, the support structure can also be shaped as a stent, i.e. as a cylindrical spiral wire prosthesis for vascular support, in order to support the position of the cardiac assist system in a blood vessel. The at least one brace can for example be the carrier of the sensor device. Additionally or alternatively, the brace can be used as a connecting element for the stent. The connection section can for example rely on a shape-lock or a friction lock to connect the device to the element of the cardiac assist system, such as a housing or a guide section. The sensor device can sense the blood stream, for example by means of thermal anemometry or by means of laser Doppler velocimetry or by means of an ultrasonic element. When the device is for example positioned in a human aorta, the sensor device can—for the purpose of determining the entire cardiac output as a blood stream—be formed to sense a pump volume flow discharged by the cardiac assist system and a residual cardiac output, for example a bypass flow through the aortic valve bypassing the cardiac assist system. The sensor device can be designed as one or multiple components. For example, the sensor device can be realized as an integrated sensor module in the form of a semiconductor chip.

According to an embodiment, the support structure can be formed as an anchoring structure for anchoring the cardiac assist system in a blood vessel. The support structure can for example be designed to anchor the device and thus the cardiac assist system connected to the device in the blood vessel with a friction lock. As an anchoring structure, the support structure can for example comprise a component with an inner diameter that is slightly larger than the inner diameter of the blood vessel in which the anchoring structure is anchored. The support structure can for example comprise at least two arc-shaped braces that have such an inner diameter in the unfolded state and can anchor the cardiac assist system, or the support structure can be formed as a stent. In this way, the anchoring structure can advantageously prevent a slippage or dislocation of the cardiac assist system. By forming the support structure as an anchoring structure, an additional component for anchoring the cardiac assist system can advantageously be omitted, which allows a compact design.

If the support structure is formed as an anchoring structure, it can according to an embodiment additionally comprise a retaining ring that is connected to the at least one brace and is designed to secure the cardiac assist system in the blood vessel with a friction lock. The retaining ring can in particular have at least one foot element or small foot for positioning the support structure. The retaining ring can for example be foldable and unfoldable for anchoring. In the unfolded state, the retaining ring can be cylindrical or conical. In addition, the retaining ring can have a shape that does not exactly correspond to the circular aortic anatomy of a human aorta. The apparatus can thus in the anchored state be held at the designated location by a radial friction lock. The foot element can have an atraumatic shape, for example, so as not to injure the blood vessel. The retaining ring can for example also comprise three foot elements that are formed to position each of the foot elements in a cusp of a heart valve. This embodiment is advantageous so as to position the apparatus and with it the cardiac assist system particularly precisely, in particular when the cardiac assist system is for example positioned and anchored behind the aortic valve by means of the device.

According to an embodiment, at least the support structure can be foldable to assume an insertion state of the cardiac assist system, and unfoldable to assume an anchoring state of the cardiac assist system. If the device is connected to the cardiac assist system, this embodiment is advantageous for the minimally invasive insertion of the cardiac assist system, for example by transfemoral access. According to this embodiment, the support structure can for example be cylindrically foldable, and in the insertion state can rest against a section of the cardiac assist system. The support structure can for example be folded such that the device along with the cardiac assist system can be inserted into a catheter for minimally invasive insertion. In the insertion state, the apparatus can correspondingly have a diameter that is less than the diameter of a human aorta. The anchored state can be understood to mean a state wherein the support structure—for example as an anchoring structure— is unfolded after insertion and alignment at the designated location in order to securely anchor the cardiac assist system to the designated location with a friction lock by increasing the diameter of the support structure.

In addition, the support structure can according to an embodiment comprise a shape memory element. The at least one brace can for example be designed as a shape memory element that advantageously allows a simple realization of the folding away action of the brace from the housing of the cardiac assist system. In addition, the entire support structure can also be formed as a shape memory element. The shape memory element can for example be made of a biocompatible shape memory polymer or a biocompatible shape memory alloy, such as Nitinol. The use of Nitinol as a shape memory material is advantageous because the Nitinol material is a proven material in the field of medicine, in particular in the field of cardiovascular medicine, for example for heart valve prostheses, stents and vascular prostheses, due to its biocompatibility and the shape memory property, which makes it possible to deploy and position even complex structures in a small installation space at the designated location.

According to an embodiment, the at least one brace can comprise at least one sensor platform. At least one sensor element of the sensor device can be arranged on the sensor platform. The brace can for example be rod-shaped and have a round or oval recess as a sensor platform, or the sensor platform can be formed as a round or oval depression. The shaping of a sensor platform on, in or of the at least one brace advantageously allows a space-saving integration of the sensor element of the sensor device and a compact design of the support structure.

Furthermore, the at least one brace can according to an embodiment comprise a line device. The line device can be configured to electrically connect at least one sensor element of the sensor device. The line device can be guided along the brace, for example. The line device can also comprise electrical contact pads that can be contacted with electrical circuit paths. Optionally, the contact pads can be arranged on the sensor platform. The line device can also be realized by electrically functionalizing at least a part of the support structure, for example when the part of the support structure is formed as a shape memory element made of Nitinol. Additionally or alternatively, the line device can comprise a correspondingly formed thin-film substrate as an electrical line.

In addition, the sensor device for sensing the blood stream can according to an embodiment comprise an ultrasonic device or an anemometry device. If the sensor device comprises an ultrasonic device, the sensor device can comprise an ultrasonic transducer, for example a bidirectional ultrasonic element, as a transmitter and receiver. In this case, the blood flow can be sensed using Doppler ultrasonic metrology. The measurement can for example be carried out within the device at a location where the at least one brace causes no turbulence in the blood stream in the implanted state of the device. If the sensor device comprises an anemometry device, the blood stream can for example be sensed by means of thermal anemometry or laser Doppler anemometry (laser Doppler velocimetry).

If the sensor device according to an embodiment comprises the anemometric device, the anemometric device can comprise a heating element and a temperature sensor. Alternatively, the anemometry device can comprise a light source and a photodiode. The heating element can for example be a heating filament. The temperature sensor can for example be a reference blood temperature sensor. In addition, the temperature sensor can also be arranged at the tip of the cardiac assist system, for example when the head unit comprises a sensor assembly with a temperature sensor at the tip of the cardiac assist system. An analysis unit of the anemometry device can, for example, detect the energy dissipation of the blood, for example on a heated second temperature sensor. In this case the heating element can for example be used as a second temperature sensor, or the heating element can for this purpose be thermally connected to a second temperature sensor. The heating element can for example be arranged on the at least one brace, and the second temperature sensor can additionally or alternatively be arranged on or below or in the heating element on the brace. If the anemometry device comprises a light source and a photodiode, the light source can be a laser, for example a so-called vertical cavity surface emitting laser. Due to the optional arrangement of the sensor device in the middle of the flow of the blood stream, the optical measuring window is advantageously additionally protected against tissue deposits.

A cardiac assist system is also proposed. The cardiac assist system has a head unit, an inlet section adjoining the head unit for introducing a blood stream, a guide section adjoining the inlet section for guiding the blood flow, an outlet section adjoining the guide section for discharging the blood flow, a housing adjoining the outlet section, a drive device arranged in the housing, and a supply cable for electrically contacting the cardiac assist system, as well as an embodiment of the device proposed above for determining a cardiac output for a cardiac assist system. The cardiac assist system can for example be formed as a left ventricular cardiac assist system. The cardiac assist system can for example be formed for positioning the cardiac assist system in the area of a human aorta. The cardiac assist system can thus be advantageously used to determine the cardiac output in a fully implanted cardiac assist system. This is advantageous in order to, for example, enable continuous measurement of the cardiac output for monitoring and assisting the human cardiovascular system by the cardiac assist system when the cardiac assist system is operated in the implanted state.

According to an embodiment of the cardiac assist system, at least one sensor element of the sensor device of the device can be arranged in the head unit of the cardiac assist system and at least one further sensor element of the sensor device can be arranged in the support structure of the device. If the sensor device for example comprises an anemometry device with a heating element and a temperature sensor, the temperature sensor can for example be arranged in the head unit of the cardiac assist system and the heating element can be arranged in the support structure of the device. This arrangement advantageously allows a compact design. Alternatively, the sensor element and the further sensor element can be arranged on different braces. For example, an anemometry sensor can be arranged on one brace and a reference sensor on another brace.

By using a previously mentioned embodiment of the device, a cardiac output can be advantageously determined.

A method for determining a cardiac output using a previously mentioned embodiment of the device is proposed. The method includes the following steps:

provide a control signal, wherein the control signal is formed to control the sensor device for sending an excitation signal for sensing the blood stream;

receive a sensor signal provided by the sensor device; and determine the cardiac output using the sensor signal.

The steps of the method can for example be carried out using a control device of the device. In the present case, a control device can be understood to mean an electrical circuit that processes sensor signals and outputs control signals and/or data signals as a function thereof.

The control device can be designed separately from the sensor device or can be integrated into the sensor device.

BRIEF DESCRIPTION OF THE DRAWINGS

Exemplary embodiments of the approach proposed here are shown in the drawings and explained in more detail in the following description. The drawings show in:

FIG. 5 a flow diagram of a method for determining a cardiac output according to an exemplary embodiment.

DETAILED DESCRIPTION

The following description of favorable exemplary embodiments of the present invention uses the same or similar reference symbols shown in the various figures for elements that act in similar ways, wherein a repeated description of these elements is omitted.

Figure 1:
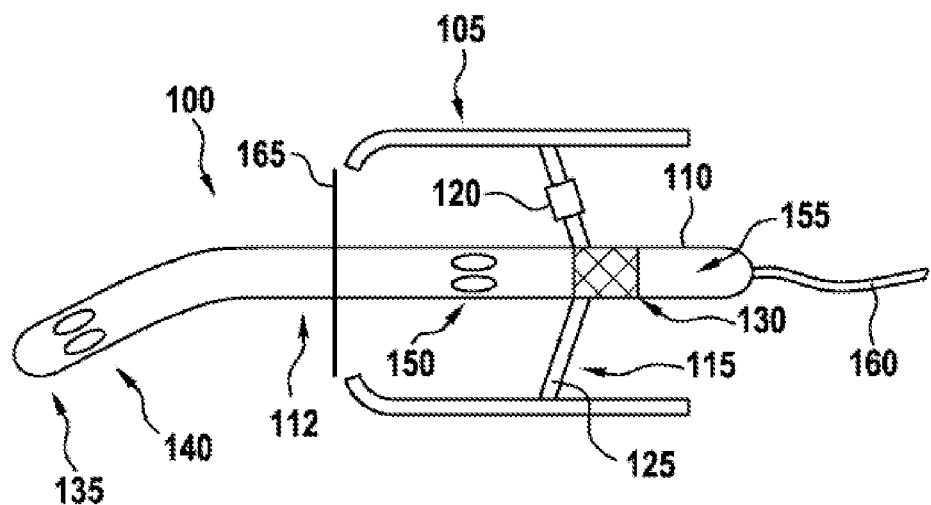
FIG. 1 a schematic illustration of a cardiac assist system with a device for determining a cardiac output according to an exemplary embodiment.

FIG. 1 shows a schematic illustration of a cardiac assist system 100 with a device 105 for determining a cardiac output according to an exemplary embodiment. The figure shows a side view of the cardiac assist system 100, which is for example designed as a left ventricular cardiac assist system having an elongated shape. The device 105 is connected to an element of the cardiac assist system. The element is, in the example shown here, designed as a section of a housing 110 of the cardiac assist system 100; alternatively, the element can also be a guide section 112 of the cardiac assist system 100.

According to an exemplary embodiment, the device 105 has a support structure 115 and a sensor device 120. The support structure 115 comprises at least one brace 125 and a connection section 130 for connecting the device 105 to an element 110 of the cardiac assist system 100. The at least one brace 125 is connected to the connection section 130 and can be folded away from the element 110. The sensor device 120 is coupled to the at least one brace 125 and is configured to sense a blood stream.

According to an exemplary embodiment, the cardiac assist system 100 comprises a head unit 135, an inlet section 140 adjoining the head unit 135 for introducing a blood stream, the guide section 112 adjoining the inlet section 140 for guiding the blood stream, an outlet section 150 adjoining the guide section 112 for discharging the blood stream, a housing adjoining the outlet section 150, a drive device 155 arranged in the housing, and a supply cable 160 for electrically contacting the cardiac assist system 100, as well as the device 105.

If the cardiac assist system 100 is implanted as a left ventricular cardiac assist system in a human aorta, the inlet section 140 is arranged in a left ventricle. There, the blood is sucked in from the ventricle, guided through the guide section 112, and discharged into the aorta by the outlet openings of the outlet section 150. The line 165 identifies the valve plane of an aortic valve. In the implanted state of the cardiac assist system 100, the aortic valves are located in the area marked by line 165 and separate the aortic and ventricular areas. To secure the described position of the cardiac assist system 100 in the implanted state, the device 105 optionally comprises an anchoring structure as a support structure 115, as described with reference to the following FIG. 2.

According to an exemplary embodiment, the sensor device 120 comprises an ultrasonic device or an anemometry device for sensing the blood stream. The anemometry device optionally comprises a heating element and a temperature sensor, or the anemometry device comprises a light source and a photodiode. The mentioned elements are optionally arranged in the support structure 115, for example on the at least one brace 125, as described with reference to FIG. 4.

Figure 2:
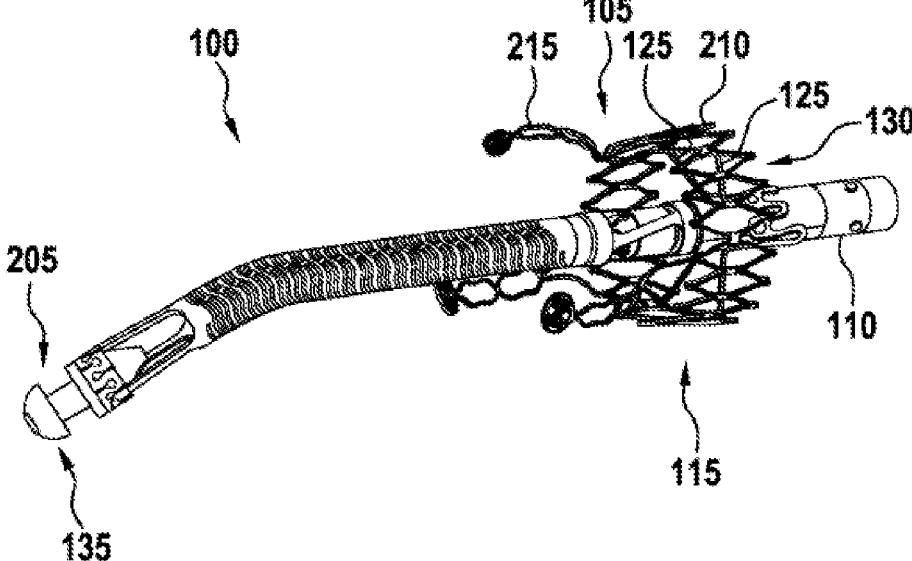
FIG. 2 a schematic illustration of a cardiac assist system with a device for determining a cardiac output according to an exemplary embodiment.

FIG. 2 shows a schematic illustration of a cardiac assist system 100 with a device 105 for determining a cardiac output according to an exemplary embodiment. A side view of the cardiac assist system 100 is shown, which essentially corresponds to the cardiac assist system described in FIG. 1 above, with the exception of the supply cable not shown here and the shaping of the support structure 115 and the head unit 135. The cardiac assist system 100 is shown here as a left ventricular cardiac assist system 100 for the aortic valve position. According to the exemplary embodiment shown here, the support structure 115 is formed as an anchoring structure 115 for anchoring the cardiac assist system 100 in a blood vessel, and is accordingly assigned the same reference symbol 115. The anchoring structure 115 can also be referred to as a stent and can also be used to position and secure the cardiac assist system 100 in the area of the aorta when implanting the cardiac assist system 100.

According to an exemplary embodiment, the support structure 115 comprises a shape memory element. The support structure 115 is in this case for example formed as an anchor structure 115 made of Nitinol, a highly elastic nickel-titanium shape memory alloy. As a connection section 130, the anchor structure 115 in this case comprises a laser-cut clip that secures the anchor structure 115 on the housing 110 in the area of the drive of the cardiac assist system.

The head unit 135 in this case comprises a sensor assembly 205. According to an exemplary embodiment, at least one sensor element of the sensor device of the device 105 described with reference to FIG. 1 is arranged in the head unit 135 of the cardiac assist system 100, for example as part of the sensor assembly 205. At least one further sensor element of the sensor device is arranged in the support structure 115 of the device. Alternatively, the entire sensor device is arranged in the support structure 115.

According to the exemplary embodiment shown here, the anchor structure 115 comprises a retaining ring 210. The retaining ring 210 is connected to the at least one brace 125 and is designed to secure the cardiac assist system 100 in the blood vessel with a friction lock. The retaining ring 210 comprises in particular at least one small foot 215 for positioning the anchoring structure 115. Two arched small feet 215 are shown here as an example. The anchoring structure 115 can optionally be folded together to assume an insertion state of the cardiac assist system 100, and can be unfolded to assume an anchoring state of the cardiac assist system 100. Here, the anchoring structure 115 is shown by way of example in the unfolded state, which corresponds to an anchoring state when the cardiac assist system 100 is anchored in a blood vessel, for example in the aorta. The anchoring structure 115 in this case comprises by way of example a plurality of evenly spaced braces 125, which are folded away from the housing 110 of the cardiac assist system 100, corresponding to the unfolded state of the anchoring structure 115. For this purpose, the at least one brace 125 is optionally formed as a shape memory element and has a pre-formed shape in order to apply an outward spring pressure and thus to press the retaining ring 210 against the vessel wall of the blood vessel. The retaining ring 210 optionally also has a pre-formed shape in order to apply a spring force against the aortic wall in the anchored state. In addition, the anchoring structure optionally comprises three small feet 215, which can be positioned in the pockets above the aortic valves and further secure the position of the cardiac assist system 100, hereinafter also referred to as pump.

According to an exemplary embodiment, the anchoring structure 115 shown here comprises the sensor device as an integrated metrology unit. At least one sensor element of the sensor device is optionally arranged on the at least one brace 125 and in this case is advantageously located in the blood stream of the total cardiac output in the aorta in order to sense the blood stream when the cardiac assist system 100 is implanted. Suitable metrology methods of the sensor device for example include heating filament anemometry or Doppler ultrasound, as described with reference to the following FIGS. 3 and 4.

Figure 3:
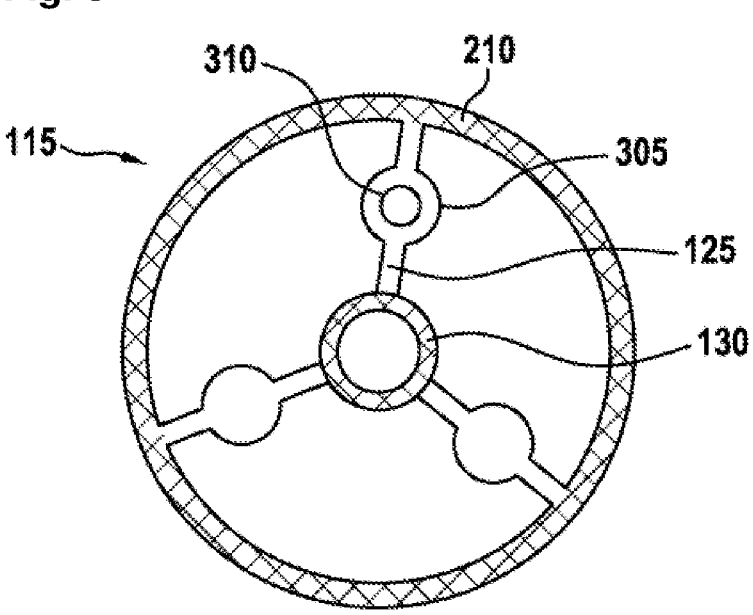
FIG. 3 a schematic illustration of a support structure of a device for determining a cardiac output according to an exemplary embodiment.

FIG. 3 shows a schematic illustration of a support structure 115 of a device for determining a cardiac output according to an exemplary embodiment. A top view onto a cross-section of the support structure 115 is shown. The support structure shown here is similar or corresponds to the support structure as described above in FIG. 2, with the exception of the shaping of the at least one brace 125, and comprises the retaining ring 210 and the connection section 130. The support structure 115 in this case for example comprises three braces 125.

According to the exemplary embodiment shown here, each brace 125 comprises a sensor platform 305. At least one sensor element 310 of the sensor device described in FIG. 1 is arranged on the sensor platform 305. Alternatively, the entire sensor device is arranged on the sensor platform 305. The integration of sensors along the brace 125, for example on the sensor platform 305, is advantageous with regard to a compact design. An ultrasonic transducer or a sensor of an anemometry device as described with reference to the following FIG. 4 can for example be arranged on the sensor platform 305 as a sensor element 310 of the sensor device. The sensor platform 305 in the example shown here has a round shape and is formed as a recess of the brace 125 at about halfway of the longitudinal extension of the brace 125 in relation to the distance of the connection section 130 from the retaining ring 210.

Figure 4:
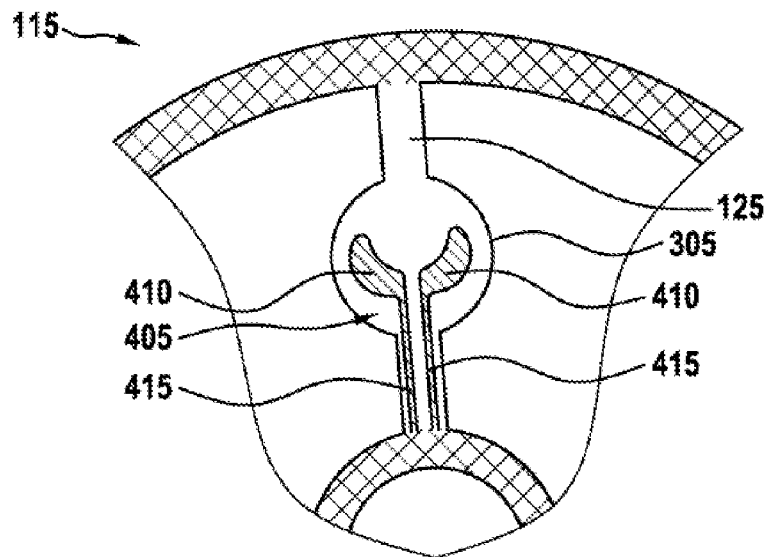
FIG. 4 a schematic illustration of a part of a support structure of a device for determining a cardiac output according to an exemplary embodiment.

FIG. 4 shows a schematic illustration of a part of a support structure 115 of a device for determining a cardiac output according to an exemplary embodiment. The figure shows a section of the support structure 115, as described with reference to FIG. 3, wherein the brace 125 according to the exemplary embodiment shown here additionally comprises a line device 405. The line device 405 is configured to electrically contact at least one sensor element of the sensor device. The line device can for example be formed to electrically contact the ultrasonic transducer as a sensor element of the sensor device. The sensor element or the entire sensor device can for example be supplied with electrical energy by the line device 405, and additionally or alternatively be connected to a control device or a communication device for data transmission.

In the example shown here, the line device 405 is shown as a two-pole electrical power supply and comprises two contact pads 410 integrated on the sensor platform 305, which are contacted with electrical circuit paths 415. The electrical conductive structure is optionally realized by electrically functionalizing the support structure 115 formed according to an exemplary embodiment as a shape memory element made of Nitinol. Alternatively, the electrical functionalization occurs by applying a separate conductor structure adapted in the shape of the support structure 115, for example by a thin-film substrate as an electrical line.

A previously mentioned exemplary embodiment of the device is advantageously used to determine the cardiac output, wherein the blood flow velocity is measured by means of thermal anemometry, laser Doppler velocimetry or Doppler ultrasound, depending on the exemplary embodiment. According to an exemplary embodiment, the sensor device comprises an anemometry device, which optionally comprises a heating element and a temperature sensor. At least one heating filament can be integrated as a heating element along the brace 125, for example on the sensor platform 305. The heating element and the temperature sensor can be arranged together on a brace 125 or on different braces 125, so that the temperature sensor can be located on a brace 125 and the heating element can be located on another brace 125. The sensor device can thus be distributed over a plurality of braces 125. In addition, a reference blood temperature sensor is optionally integrated on the sensor platform 305 as a temperature sensor. Such a reference blood temperature sensor can also be arranged on another brace 125. Alternatively, the temperature sensor is positioned in the head unit in the tip of the cardiac assist system. An analysis unit in this case detects the energy dissipation (comparable to a coolant flow) of the blood past a heated anemometry sensor. The heating filament is optionally formed as a second temperature sensor or another temperature sensor is thermally connected to the heating filament and arranged on, below, or in the heating filament on the brace 125.

In order to determine the cardiac output by means of laser Doppler velocimetry, the anemometry device comprises a light source such as a laser and a photodiode. The light source and the photodiode are optionally integrated on one or more sensor platforms 305. This is advantageously space-saving and allows the metrology to be thermally decoupled from the drive.

Alternatively, the sensor device for determining the cardiac output by means of Doppler ultrasound comprises an ultrasonic device that is suitable for flow measurement. Sound impulses are emitted by an ultrasonic transducer and the phase propagation of the backscattered sound impulse is analyzed. The pulsed-wave Doppler method allows a purposeful selection of the analysis depth; the measurement is for example taken further away from the brace 125, so that turbulence induced by the brace 125 cannot be detected. The ultrasonic device optionally comprises a bidirectional ultrasonic element for the transmitting and receiving direction. In this case, the ultrasonic transducer or the bidirectional ultrasonic element is arranged on the support device as the sensor element of the sensor device, and is optionally integrated on the brace 125 or the sensor platform 305.

Figure 5:
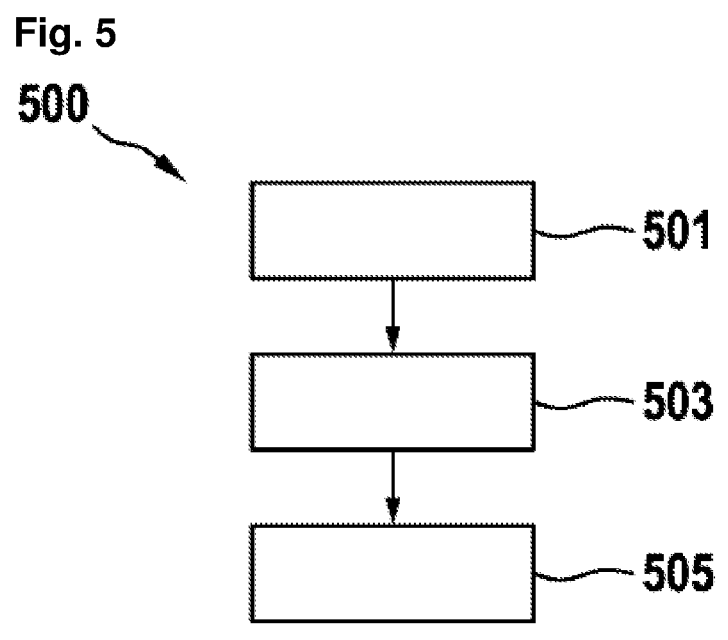

FIG. 5 shows a flow chart of a method 500 for determining a cardiac output using an exemplary embodiment of the aforementioned device. The method 500 comprises provisioning as a step 501, receiving as a step 503, and determining as a step 505. The provisioning step 501 provides a control signal, which is designed to control the sensor device, as is for example described with reference to FIG. 1, for sending an excitation signal for sensing the blood stream. The receiving step 503 involves receiving a sensor signal provided by the sensor device. The determining step 505 involves determining the cardiac output using the sensor signal.

The invention claimed is:

1. A device for determining a cardiac output of a patient having a cardiac assist system, the device comprising:
a support structure comprising:
an anchoring structure;
at least one brace; and
a connection section configured to connect the device to an element of the cardiac assist system, wherein the at least one brace is positioned between the anchoring structure and the connection section, and is configured to move away from the element from a first position to a second position; and
a sensor device coupled to the at least one brace at a position located between the connection section and the anchoring structure and configured to sense a blood stream flowing past the at least one brace;
wherein the at least one brace extends at least partially radially outward from the element in the second position.

2. The device of claim 1, wherein the support structure is configured to anchor the cardiac assist system in a blood vessel.

3. The device of claim 2, wherein the support structure comprises a retaining ring configured to connect to the at least one brace and to secure the cardiac assist system in the blood vessel with a friction lock.

4. The device of claim 1, wherein the support structure is configured to transition between an insertion state and an anchoring state, and wherein the support structure is in a folded configuration when in the insertion state and is in an unfolded configuration when in the anchoring state.

5. The device of claim 1, wherein the support structure comprises a shape memory element.

6. The device of claim 1, wherein the at least one brace comprises a sensor platform, and wherein at least one sensor element of the sensor device is arranged on the sensor platform.

7. The device of claim 1, wherein the at least one brace comprises a line device configured to electrically contact at least one sensor element of the sensor device.

8. The device of claim 1, wherein the sensor device comprises at least one of an ultrasonic device or an anemometry device.

9. The device of claim 8, wherein the sensor device comprising the anemometry device, and wherein the anemometry device comprises:
a heating element and a temperature sensor; or
a light source and a photodiode.

10. A cardiac assist system comprising:
a head unit;
an inlet section adjoining the head unit and being configured to blood flow from a blood stream;
a guide section adjoining the inlet section and being configured to guide the blood flow;
an outlet section adjoining the guide section and being configured to discharge the blood flow;
a housing adjoining the outlet section;
a drive device arranged in the housing;
a supply cable configured to electrically contact the cardiac assist system; and
a device configured to determine a cardiac output, the device comprising:
a support structure comprising:
an anchoring structure;
at least one brace; and
a connection section configured to connect the device to the guide section or the housing, wherein the at least one brace is positioned between the anchoring structure and the connection section, and to move away from the guide section or the housing from a first position to a second position; and
a sensor device coupled to the at least one brace at a position located between the connection section and the anchoring structure and configured to sense the blood stream flowing past the at least one brace;
wherein the at least one brace extends at least partially radially in the second position.

11. The cardiac assist system of claim 10, wherein at least one sensor element of the sensor device is arranged in the head unit of the cardiac assist system, and wherein at least a second sensor element of the sensor device is arranged in the support structure.

12. A method for determining a cardiac output of patient having a cardiac assist system comprising:
providing a control signal, wherein the control signal is configured to control a sensor device of a device configured to determine the cardiac output to cause the device to send an excitation signal for sensing a blood stream, the device comprising:
a support structure comprising:
an anchoring structure;
at least one brace; and
a connection section configured to connect the device to an element of the cardiac assist system, wherein the at least one brace is positioned between the anchoring structure and the connection section, and is configured to move away from the element from a first position to a second position; and
a sensor device coupled to the at least one brace at a position located between the connection section and the anchoring structure and configured to sense a blood stream flowing past the at least one brace;
receiving a sensor signal provided by the sensor device; and
determining the cardiac output using the sensor signal;
wherein the at least one brace extends at least partially radially outwardly from the element in the second position.

13. The device of claim 1, wherein the element comprises a housing section or a guide section of the cardiac assist system.

14. The device of claim 3, wherein the retaining ring comprises at least one foot element being configured to position the support structure.

15. The cardiac assist system of claim 10, wherein at least one sensor element of the sensor device of the device is arranged on a first brace of the support structure, and wherein at least a second sensor element of the sensor device is arranged on a second brace of the support structure.

16. The cardiac assist system of claim 10, wherein the support structure comprises a retaining ring configured to connect to the at least one brace and to secure the cardiac assist system in a blood vessel with a friction lock.

17. The cardiac assist system of claim 10, wherein the support structure is configured to transition between an insertion state and an anchoring state, and wherein the support structure is in a folded configuration when in the insertion state and is in an unfolded configuration when in the anchoring state.

18. The cardiac assist system of claim 10, wherein the at least one brace comprises a sensor platform, and wherein at least one sensor element of the sensor device is arranged on the sensor platform.

19. The cardiac assist system of claim 10, wherein the at least one brace comprises a line device configured to electrically contact at least one sensor element of the sensor device.

* * * * *